United States Patent [19]

Coughlin et al.

[11] 4,016,293

[45] Apr. 5, 1977

[54] METHOD OF CARRYING OUT ENZYME CATALYZED REACTIONS

[76] Inventors: Robert W. Coughlin, 902 Seventh Ave., Bethlehem, Pa. 18018; Marvin Charles, 622 N. 29 St., Allentown, Pa. 18104

[22] Filed: Feb. 11, 1974

[21] Appl. No.: 441,569

Related U.S. Application Data

[63] Continuation-in-part of Ser. No. 228,748, Feb. 23, 1972, Pat. No. 3,928,143.

[52] U.S. Cl. .................. 426/42; 195/31 R; 195/115; 195/116; 426/41
[51] Int. Cl.² ............................... C12D 13/02
[58] Field of Search ............ A23C/21/00; 195/115, 195/116, 63, 68, 31 F, 31 R; 426/41, 42

[56] References Cited

UNITED STATES PATENTS

| | | | |
|---|---|---|---|
| 2,681,858 | 6/1954 | Stimpson | 426/41 |
| 3,519,538 | 7/1970 | Messing et al. | 195/63 |
| 3,705,084 | 12/1972 | Reynolds | 195/68 X |
| 3,767,535 | 10/1973 | Havewala et al. | 195/116 |
| 3,783,101 | 1/1974 | Tomb et al. | 195/63 |
| 3,804,719 | 4/1974 | Messing | 195/68 |
| 3,852,496 | 12/1974 | Weetall et al. | 195/68 X |
| 3,868,304 | 2/1975 | Messing | 195/68 X |

OTHER PUBLICATIONS

Emery et al., "Some Applications of Solid-Phase Enzymes in Biological Engineering," *Birmingham University Chemical Engineer*, vol. 22, No. 2, Summer 1971, pp. 37–41.
Barker et al., "Enzyme Reactors for Industry," *Process Biochemistry*, vol. 6, No. 10, (Oct. 1971), pp. 11–13.

*Primary Examiner*—Alvin E. Tanenholtz
*Assistant Examiner*—Thomas G. Wiseman

[57] ABSTRACT

A liquid stream containing the reactants is passed through a bed of enzyme catalyst, made up of enzymes bonded to small, dense particles of carrier or support materials, in a manner which causes the bed to expand or fluidize and a chemical reaction is thereby carried out in a process that is simultaneously free from limitations due to plugging and excessive pressure drop and which also has the advantage of the high mass transfer rates that can be realized between the liquid and small particles. Reactions are carried out in this manner using enzymes bound to porous and non-porous inorganic supporting particles. This process has been employed for treating cheese whey with the enzyme lactase in a fluidized bed of inert particles to which the lactase is bound.

14 Claims, 5 Drawing Figures

METHOD OF CARRYING OUT ENZYME CATALYZED REACTIONS

The present application is a continuation-in-part of copending U.S. patent application Ser. No. 228,748 filed Feb. 23, 1972, now U.S. Pat. No. 3,928,143.

This application is related to the following applications, all filed concurrently herewith: Method of Preparing Immobilized Enzymes, inventors Coughlin, Charles & Beard; Method of Bonding Enzymes to Particulate Supports, inventors Coughlin, Charles & Paruchuri; Method of Preparing Improved Supports for Immobilized Enzymes, inventors Coughlin, Charles & Allen.

BACKGROUND OF THE INVENTION

1. Field of Invention

This invention relates to a method for carrying out chemical reactions using as catalysts enzymes that are insolubilized of immobilized by bonding them to solid supporting materials, and in which a solution of the chemical reactants passes upward through a bed of such solid supporting material to which the enzymes of choice have been bound, such supporting material being in the form of particles of the proper size and density and the reactant solution flowing through the bed at such a rate that the bed of particles becomes expanded or fluidized and the advantages of fluidized bed operation are conferred upon the system and process thereby realized. Preferred embodiments of the present invention involve the use of stainless steel, nickel oxide and porous alumina as enzyme supports and the enzyme lactase for treating solutions of lactose and cheese whey.

2. Description of Prior Art

Within the last decade the art of attaching enzymes to insoluble supporting materials has been developed and such solid-bound enzyme catalysts can now be applied to practical, commercial processes such as producing glucose from starch, isomerizing glucose to the sweeter sugar fructose, hydrolyzing proteins and sugars, clarifying fruit juices and beer, carrying out reactions for producing antibiotic pharmaceutical reagents, treating human blood for promoting desired chemical reactions such as decomposition of urea, and many other useful and potentially useful purposes. A major advantage of using enzymes in such insoluble form bound to a solid supporting material is that the catalytically active enzyme may be physically retained in the reaction vessel and contacted there with a continuously flowing liquid process stream. Before it was possible to bond enzymes to such insoluble supports, the enzymes would remain in the liquid process stream or could be separated therefrom only with difficulty with the result that the enzyme could be reused only with difficulty or not at all. Now that the art exists for bonding enzymes to insoluble supports, it becomes possible to use them in much the same way as ordinary heterogeneous catalysts on inert, insoluble supporting carriers that are well known in the chemical process industry. Such use now permits the continuous, convenient reuse of the same insolubilized enzyme catalyst for contacting a continuously flowing liquid reaction process stream thereby catalyzing a desired chemical reaction within said stream but without the necessity of separating the enzyme from the reaction products or the possible disadvantage of losing said enzyme entirely and not being able to re-use it.

However, some major problems have been encountered in the practical application of such insolubilized enzymes. They have usually been bonded to natural and synthetic high polymers and then used in fixed bed reactors; in such systems disadvantageously high pressure drop and plugging have been encountered and this behavior can be attributed to the small particle size and to the deformable, gel-like properties of the polymeric supporting material. More recent attempts to circumvent these kinds of problems have involved using inorganic supporting materials such as apatite and glass. While the latter materials are less deformable than the organic polymeric supports, columns packed with these materials still are susceptible to plugging and cause high pressure drop when small particle sizes are used in fixed, packed beds. Moreover such materials are often either not available in large quantities of controlled properties or are very expensive. When the particles are made sufficiently large to avoid such adverse plugging and pressure-drop behavior, their very size causes large mass transfer resistances both within the liquid film surrounding the support particles and within the support particles themselves if they are porous. Such mass transfer resistance can prevent the reactants from reaching the immobilized enzyme as fast as they can react and thereby can result in inefficient utilization of the enzyme bound to the solid support. To minimize mass transfer resistances, both within the solid supporting particles themselves and in the liquid film surrounding them, the particles should be as small as possible. However, as has already been stated, fixed packed beds of small particles are markedly susceptible to plugging and cause disadvantageously high pressure drops. Stirred-tank, slurry reactors are also susceptible to plugging and have the added disadvantages of back mixing, mechanical complexity and high shear rates.

The present invention utilizes insolubilized enzymes bound to solid supporting materials in a process that simultaneously provides relative freedom from plugging and from high pressure drops, reasonably high liquid flow rates in approximate plug flow and excellent mass-and heat-transfer rates from process stream to the solid supporting particles and within the particles themselves. The present invention employs an expanded or fluidized bed of insoluble support particles to which enzyme is bound but the present invention differs from prior art in that expanded or fluidized bed processing has never before been applied to enzyme catalyzed reactions, in that the insoluble, support particles must have certain types of properties for good fluidization behavior in a fast-flowing liquid stream, in that said good fluidization properties are achieved by constructing the insolubilized-enzyme, catalyst particles in new and different ways, in that simplified enzyme binding techniques are employed and in that the support particles are inert, commercially available, reasonably priced materials of uniform and controllable properties. Additional features of the present invention reside in its application to the use of the enzyme β-D-galactosidase (lactase) for hydrolyzing the disaccharide lactose to its constituent monosaccharides glucose and galactose. A further feature of the present invention is its use in treating cheese whey to hydrolyze its constituent lactose using fluidized beds of small, dense inert particles to which the enzyme lactase is bound.

Cheese whey is the liquid remaining after the curd is separated from milk as a preliminary step in cheese manufacture. The by-product whey contains essentially all the soluble protein and minerals of the milk as well as about 5% lactose. Converting this lactose to its constituent hexoses glucose and galactose improves various properties of whey thereby making whey more valuable and more desirable for blending into food products such as processed cheese, ice cream, puddings, batters and various bakery products. Converting the lactose to glucose and galactose is desireable because the latter two sugars are sweeter, more soluble and more easily dried than lactose.

The application of fluidized bed processing to large-volume streams such as cheese whey is particularly advantageous in that impurity particles such as curd pass readily through such a bed. This behavior is a great improvement over that of fixed beds which filter and trap such particles with attendant increase in pressure drop or flow resistance and eventual plugging. Before the present invention fluidized-bed processing using immobilized enzymes has never before been applied to such processes.

SUMMARY OF THE INVENTION

It is an object of this invention to provide a means of carrying out enzyme-catalyzed reactions by a process which is not susceptible to plugging, which permits large flow rates of liquid reactant stream with low pressure drop and which employs enzymes bound to solid supporting material as carrier.

It is another object of this invention to provide a process with the above-described advantages and for the purpose stated above, that can also operate using small particles of supporting material to which enzyme catalyst is bound and which thereby provides high rates of mass transfer from the liquid stream to the enzyme catalyst particles and within these particles.

It is a further object of this invention to provide such a process that also permits approximate plug flow with little backmixing of the liquid as it flows through the bed of enzymic catalyst particles.

Still another object of this invention is to provide insolubilized enzyme catalysts having properties of density and particle size suitable for conducting such processes as described above.

Yet another object of this invention is to provide methods of preparing insolubilized enzyme catalysts possessing such properties.

An additional object of the present invention is to provide rapid and simplified methods for bonding enzymes to readily available, reasonably priced, small, inert dense particles of controlled properties, such as particles of alumina, of nickel oxide or of stainless steel.

Yet another object of the present invention is to provide a process for converting lactose in aqueous solutions thereof, such as cheese whey, utilizing a fluidized bed of inert particles to which the enzyme lactase has been bound by rapid and simple methods.

These and other objects have now herein been attained by a process in which the enzymes are insolubilized by binding them to the surfaces of porous or non-porous, dense, inorganic particles, or to a thin layer of porous material supported on the outside surfaces of such non-porous particles, passing a steady stream of liquid reactant through a bed of such particles, the flow rate, viscosity and density of the liquid and the sizes and densities of the particles being of the values required to cause expansion or fluidization of the bed of particles and thereby providing the benefits of fluidized or expanded bed operation with a liquid stream flowing in approximate plug flow through the fluidized or expanded bed. Said process has been successfully applied to the hydrolysis of cheese whey and lactose solutions using the enzyme lactase.

DEFINITIONS

Within this disclosure, the term expanded bed refers to a process wherein the particles of the bed are suspended and agitated by the liquid but do not mix or circulate within the bed to any appreciable extent, the term fluidized bed to a process wherein the suspended and agitated particles do circulate and mix within the bed, and the term suspended bed is generic to the terms fluidized bed and expanded bed and used to refer to either one or both of them. The term enzyme as used within this Application can refer to an enzyme, a co-enzyme or an enzyme-analogue (which is a molecule synthesized to approximate the catalytically active structure of a natural enzyme and which has similar catalytic activity). The terms immobilized and insolubilized are used interchangeably throughout this disclosure to denote either chemical or physical binding of an enzyme to a carrier or entrapment of an enzyme within a carrier. The term lactase unit (LU) used in this disclosure is defined as that enzymic activity which will produce $3.3 \times 10^{-8}$ moles of glucose per minute by hydrolyzing a like amount of lactose at pH = 3.5 and lactose concentration = 20% by weight at a temperature of 37° C.

DESCRIPTION OF PREFERRED EMBODIMENTS

Figure 3:
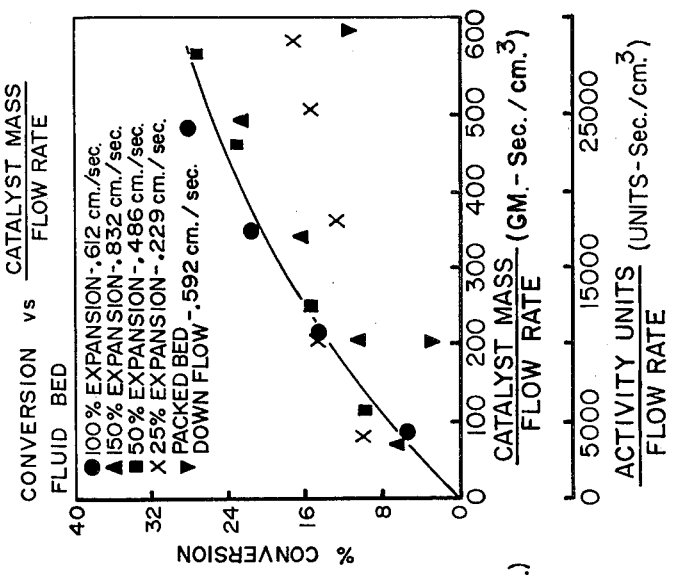

The embodiments discussed here are presented herein for purposes of illustration only and are not intended to be limiting in any manner.

According to the present invention, one of the important properties of a useful insolubilized enzyme catalyst support or carrier is a density sufficiently large to permit the use of small particles and large liquid flow rates in expanded- or fluidized-bed operation. Although insolubilized enzymes have been known or used for more than a decade, they have seldom if ever been employed in expanded or fluidized bed processes; one reason for this undoubtedly is the fact that in almost every instance the enzymes have been bound to materials of low density. The present invention calls for the use of particles of inert, high density materials such as non-corrodible metals or metal oxides as supporting material to which the enzyme or enzymes of choice are then bound.

The carrier or support for the enzymes as used in this invention can be particles of metallic nickel or nickel oxide sinter as supplied by the International Nickel Company, Inc. under the trade names Nickel Oxide Sinter 75 and Nickel Oxide Sinter 90. The density of this material is about 8 gm/cm$^3$ and an appropriate particle-size size range is 10μm to 0.25 inch for fluidization by water, although the preferred size range will depend on the density and viscosity of the fluidizing liquid. Another useful support for fluidized bed operation is fine, particulate stainless steel such as the (316-L-Si) stainless steel powder (of size range 149 μm to 105 μm) supplied by Glidden Metals, Cleveland, Ohio. Still another suitable support is the porous alumina particles of size range 250–150 μm, specific surface area = 4 m$^2$/gm and mean pore diameter 0.44 μm as supplied by the Carborundum Company, Latrobe, Pa.

(catalyst support SAEHS-33). These supports have been used by us in practicing the present invention.

A particularly effective, simple and low-cost technique of enzyme binding employed by us in practicing the present invention is to contact the carrier particles with a solution of the enzyme-to-be-bound thereby causing the enzyme to sorb on said particles. After sorption the enzyme-bearing particles are treated with a bifunctional reagent such as glutaraldehyde which is believed to react with free amino groups along the polypeptide chain of the enzyme; this treatment cross links sorbed enzyme molecules thereby fixing them in place. We have also found that such crosslinking can stabilize enzyme activity over wider ranges of pH as compared to the free enzyme. We have also found that particles of relatively low surface area can be coated with a porous coating of a metal oxide such as titanium oxide by simply adding $TiCl_4$ to an aqueous suspension of the particles; the $TiCl_4$ hydrolyzes producing titanium oxide which is deposited in a thin porous layer of high surface area on the particles. In this way we have coated stainless steel particles with titanium oxide coatings that were readily visible under the electron microscope; particles so treated show a greatly enhanced ability to sorb enzyme and the enzyme appears to be so strongly sorbed within the porous coating that it does not wash off. For enzymes sorbed on such materials crosslinking does not produce great increases in ability to withstand desorption but it is still desireable to treat such preparations with a crosslinking agent to enhance enzyme stability.

There are many other ways of depositing porous, high-surface-area coatings on suitable carrier particles. For example, a procedure parallel to that immediately above may be employed to produce coatings of tin, vanadium, aluminum or zirconium oxides by using the respective chloride salts of these elements.

It is evident that many kinds of physical and chemical bonds can be employed to attach enzymes to a dense, particulate carrier suitable for expanded-or fluidized-bed operation without departing from the substance of the present invention. For example various techniques for bonding a variety of enzymes to inorganic carriers using silane coupling agents have been disclosed and claimed in U.S. Pat. No. 3,519,538 granted to Messing et al. The various types of chemical bond that have been successfully employed are part of the established art and are described in published literature [e.g. Kay, Process Biochemistry 3, 36 (1968) and Brown et al, Enzymologia 35, 215 (1968)]. It is also evident that it is possible to practice the present invention using various other types of dense particulate material to which the enzyme of choice is then bound. By proper selection of these materials it is possible to vary the density of the insolubilized enzyme catalyst particles over a wide range; for example it is possible to use alumina, (density 2.5 $gm/cm^3$), nickel (density 8.9 $gm/cm^3$), iron or preferably stainless steel (density about 8 $gm/cm^3$), silver (density 10.5 $gm/cm^3$), molybdenum (density 10.2 $gm/cm^3$), tantalum (density 16.6 $gm/cm^3$), gold or tungsten (density 19.3 $gm/cm^3$), rhodium (density 21.4 $gm/cm^3$), platinum (density 21.5 $gm/cm^3$) and various alloys of these metals. Clearly, the metals, alloys or similar materials should also be chosen for inertness, resistance to the particular aqueous environment to be employed and for properties of non-interference with the particular enzyme and chemical reaction system to be employed. It is evident that a wide variety of materials can be used for these carrier particles.

When it is possible to form a tough, tenacious, insoluble and otherwise suitable oxide coating on metallic particles of the proper density, the enzyme of choice can be bound to the oxide by a silane coupling technique as mentioned above, in which the oxide is silanized to produce alkylsilane groups on the surface as a first step. It is clear that it is also possible to use particles of the metal oxide itself as the carrier material using the silane procedure. Another possible approach, however, is to first coat the particles with a suitable polymer and then use one of the many known techniques for chemically bonding the enzyme of choice to the polymer. These techniques for bonding enzymes to polymers, which are part of the established art, have been discussed by Goldstein and Katchalski [Zeitschrift fur analytische Chemie 243, p. 375 (1968)] and Manecke [Proceedings of the Biochemical Society, page 2 P, (January 1968)] and they include the use of derivatives of polymers such as cellulose, polystyrene, copolymers of leucine and phenylalanine, copolymers of methacrylic acid, methylacryl-3-fluoroanilide and divinyl benzene, copolymers of methacrylic acid, fluorostyrene and divinyl benzene, polymers of m-isothiocyanatostyrene and vinylisothiocyanate and chemical bonds such as azide, diazo, isocyanato, isothiocyanato, carbodiimide and sulfonamide; enzymes that have been bound by these techniques include glucose oxidase, papain, ficin, trypsin, urease, diatase, invertase, chymotrypsin and alcohol dehydrogenase. An alternative but similar approach is to coat the dense carrier particles with glass by using the fine particle glazes and sealants supplied by Owens-Illinois and by Corning Glass and then to bond the enzyme of choice to this glass layer using one of the techniques described above for bonding enzymes to metallic oxides that begins by refluxing the glass-coated particles with a toluene solution of γ-aminopropyltriethoxysilane. However, none of the techniques mentioned in this paragraph appear to be as simple, straight-forward and low in cost as the techniques of sorption or sorption combined with crosslinking which we have employed in the practice of the present invention and which are further described in the Examples which follow.

Preparation of enzyme catalysts immobilized by bonding to dense particles as described herein permits their use in expanded-bed or fluidized-bed reactors in which the particles are maintained in fluidized suspension by the flow of a stream of liquid (which contains the substrate or reactant) through the bed. Such liquid fluidization provides the advantages of approximate plug flow of the liquid through the bed in contrast to a stirred, slurry-type reactor and also relative freedom from plugging and from high pressure drop in contrast to fixed-bed operation. In the usual type of fluidized operation the fluidized particles will be well mixed within the bed but it is possible to avoid the mixing of the particles from one part of the bed to another by packing the bed with larger particles which do not move or mix themselves and thereby prevent the small enzyme-bearing particles from mixing within the bed, but at the same time permit the fluidization of the small particles within the interstices of the packed large particles. Such packed, fluidized beds which are described by Gabor [Chem.Eng.Progr.Symp.Series, No. 62, 62, 302 (1966)] and Gabor et al. [Chem.Eng.Progr- .Symp.Series No. 42, 60, 96 (1964)] also fall within the purview of the present invention.

The use of dense materials for the particles which carry the enzyme permits good fluidization while using particles of small size; using such small particles increases mass-transfer rates of reactants to the particles and therefore also increases the rate of chemical reaction. Furthermore, the use of dense, enzyme-carrier particles has the added advantage of permitting high liquid flow rates through the expanded- or fluidized-bed without entrainment and loss of the particles from the bed. The higher liquid flow rates and higher rates of reaction that can be realized in this kind of system using small, dense particles as catalyst carrier provides still another important advantage of high production rate of reaction product from this type of reactor. These and other advantages will be more apparent from the examples which follow.

Having generally described the invention, a further understanding can be obtained by reference to certain specific examples which are presented herein for purposes of illustration only and are not to be limiting in any manner.

EXAMPLES

The superiority of suspended-or fluidized-bed, immobilized-enzyme reactors is demonstrated herein by experiments in which lactase and other enzymes are bound to dense, inert, insoluble particles by simplified, low-cost techniques; the enzyme-bearing particles are then employed in fluidized-bed reactors. Reactors using the enzyme lactase are employed to convert to simpler sugars the lactose in cheese whey and in aqueous lactose solutions. Example V below demonstrates the binding of the enzyme amyloglucosidase to dense, inert particles of stainless steel and alumina. The resulting immobilized amyloglucosidase particles can be used to hydrolyze solutions of starch and other polysaccharides in fluidized- or suspended-bed reactors.

EXAMPLE I 100 gm of International Nickel Co. Sinter 90 (nickel oxide particles; 35–80 mesh sieve size) in 300 ml $H_2O$ were placed in a flask and chilled in an ice bath. To this mixture 65 ml of $TiCl_4$ was slowly added. After addition of $TiCl_4$ the mixture was heated at 80° C for about 30 min., following which the Sinter 90 particles were separated and washed thoroughly to remove non-adhering fine particles of precipitated titanium oxide. It has been found that such treatment or activation of carrier particles with water and a hydrolyzable metal salt (such as $TiCl_4$) can increase their specific surface area by about ten times, thereby rendering the particles much better sorbents for enzymes. The treated Sinter 90 particles were then contacted with a buffered solution of lactase [$\beta$-D-galactosidase produced from Aspergillus niger, purchased from the Wallerstein Company, Morton Grove, Ill.] in the following proportions:

1 gm treated Sinter-90, 3 ml citrate-phosphate buffer (pH = 4.0) and 24 mg of the lactase The resulting mixture was maintained at 5° C for about 12 hours and then the Sinter-90 particles were separated and washed with buffer solution; these particles then displayed a specific enzymatic activity of about 100–300 lactase units (LU) per gm. Higher specific enzymatic activity could be obtained by various means such as simply increasing the proportion of enzyme in the contacting phase of this procedure. Similar results were obtained by applying essentially the same procedure to coat stainless steel particles (149–105 $\mu$m particle size — obtained from the Glidden Corporation) and then contacting with enzyme in the same way. It has also been found that subsequent treatment of these particles with glutaraldehyde does not affect specific enzymic activity but such treatment can improve the stability of the bound enzyme. Enzymatic activities of lactase preparations were assayed by measuring the conversion of lactose to glucose using the Glucostat analysis kit supplied by Worthington Biochemical Corporation, Freehold, N. J.

The Sinter-90 particles as described above were packed in a 1-inch diameter column to a bed height of about 7.6 cm and the resulting device used to treat a solution of lactose (~20 mg/ml) in citrate-phosphate buffer (pH —3.6) at a temperature of 30° C and at flow rates ranging from about zero to 4 ml/sec-$cm^2$ of column cross sectional area (i.e. at superficial velocity of about 0–4 cm/sec). Various conversions of lactose to glucose were obtained depending on flow rate or space time in the reactor and the results are plotted in FIG. 1 as percentage conversion vs (activity units/flow rate), the abscissa being proportional to space time or residence time in the reactor. Conversions were computed from glucose concentrations of the feed and effluent of the column; glucose concentration was measured by the glucose oxidase method using the Glucostat reagent kit supplied by Worthington Biochemical Corporation.

Figure 2:
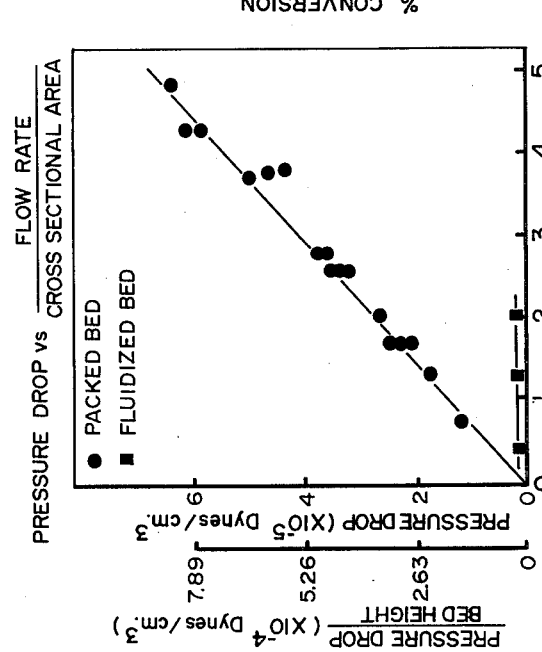
Figure 1:
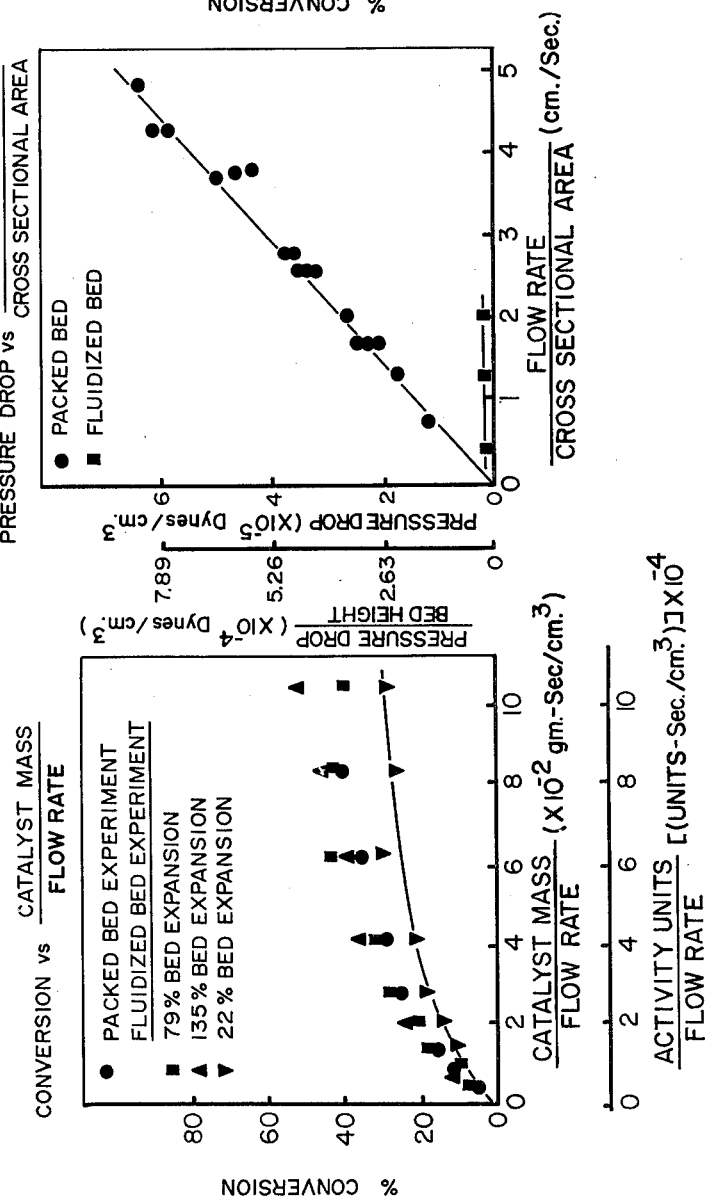

The column containing particles of immobilized lactase was operated in the fixed-bed mode using downflow with results indicated in FIG. 1 by circular data points and in the fluidized-bed mode using upflow with corresponding results indicated on FIG. 1 by square data points (for 79% bed expansion) and triangular data points (apex of triangle pointing upwards for 135% bed expansion and apex of triangle pointing downwards for 22% bed expansion). The superiority of fluidized-bed operation with large bed expansion is evident from FIG. 1. Pressure drop vs flow rate data were also obtained for the column reactor of the present Example and the results are shown plotted in FIG. 2 as pressure drop per unit bed height vs flow rate. From FIG. 2 it is evident that operation in the fluidized-bed mode produces far lower pressure drop (square data points) than operation in the fixed-bed mode (circular data points).

EXAMPLE II

Glidden stainless steel powder (105–149 $\mu$m) was contacted at room temperature with solutions of Wallerstein lactase LP enzyme in citrate-phosphate buffer (pH=3.5) for about ½ hour with gentle agitation. The steel powder was then separated from the enzyme solution and then contacted at room temperature with a 5% solution of glutaraldehyde in citrate-phosphate buffer (pH=5) for about 80 min. with gentle agitation. After removal from the glutaraldehyde solution the steel powder was recontacted for 30 min. with the original enzyme solution at room temperature with gentle agitation. The concentrations and proportions of solutions used for two typical preparations were as follows:

| PREPARATION | ENZYME SOLUTION CONCENTRATION | ENZYME SOLUTION PROPORTION | GLUTARALDEHYDE SOLUTION PROPORTION | RESULTING ACTIVITY |
| --- | --- | --- | --- | --- |
| A | 8 mg/ml | 2ml/gm of steel | 2ml/gm of steel | 95LU/gm |
| B | 16 mg/ml | 1.2ml/gm of steel | 2ml/gm of steel | 237LU/gm |

Figure 4:
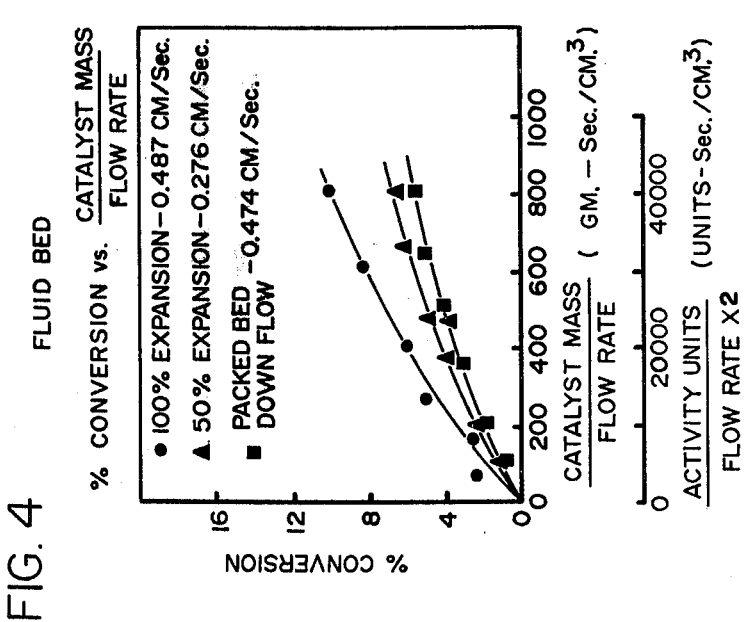

It was found, as suggested by the activities of the two preparations detailed above, that the specific activity of the resulting immobilized enzyme bound to steel could be increased by increasing the enzyme concentration of the contacting solution. Fixed-bed and fluidized-bed experiments carried out with lactase immobilized on stainless steel prepared as described under this Example gave conversions which are plotted in FIGS. 3 and 4. FIG. 3 shows results using a lactose solution of 0.18 mg/ml and FIG. 4 shows results obtained with cheese whey obtained from the LeHi Dairy, Allentown, Pa. For each of these feed streams fixed-bed and fluidized-bed operation was employed in the same column; several different bed expansions were employed for fluidized operation as indicated on the graphs of FIGS. 3 and 4. As in the case of FIG. 1 for Example I; the results plotted in FIGS. 3 and 4 indicate superiority for fluidized-bed operation at large bed expansions.

EXAMPLE III

Porous alumina (Carborundum Company catalyst support SAEHS-33) was sieved to —40/+80 mesh (170–420 μm) and contacted sequentially with lactase and glutaraldehyde solutions as in Example II using similar pH, temperatures, times, etc. Solution concentrations, proportions and resulting specific activity were as follows:

| ENZYME SOLUTION CONCENTRATION | ENZYME SOLUTION PROPORTION | GLUTARALDEHYDE SOLUTION PROPORTION | RESULTING ACTIVITY |
| --- | --- | --- | --- |
| 20 mg/ml | 2.5 ml/gm alumina | 2.5 ml/gm alumina | 2650 LU/gm |

Figure 5:
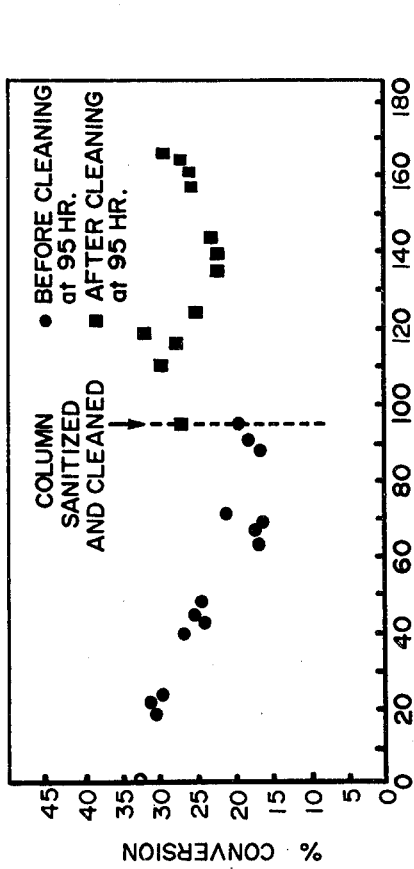

Immobilized lactase sorbed and crosslinked on alumina as described above was placed in a 1-inch. i.d. column and used to process cheese whey in the fluidized bed mode at 50° C. Conversions for a 31 cm bed (measured unexpanded) and flow rates of 85–95 ml whey per min ranged from about 35 to 15% over a period of about 170 hours on stream. The conversions vs on-stream time are shown plotted in FIG. 5.

The binding techniques of the examples above have also been applied successfully to bonding to the same supports the following additional enzymes: asparaginase, alpha amylase, glucoamylase, pepsin, catalase and glucose oxidase.

In addition the enzyme-binding technique (i.e. sorption of enzyme or sorption of enzyme followed by cross-linking) has been achieved by placing the enzyme support in a reactor and simply pumping the enzyme solution and the glutaraldehyde solution in the proper sequence through the bed; it is often most advantageous to do this with the bed operating in the fluidized mode. Moreover, we have also found that these immobilized enzymes can be regenerated by heating them at about 1000° F sufficiently long (about 30 min) to destroy and evaporate organic matter (leaving behind essentially support alone) and then recontacting the support (after cooling) with the appropriate enzyme and cross-linking solutions. The technique of sorption, or sorption followed by crosslinking has been used to attach enzymes to the following additional support materials: glass, pumice, iron oxide, silica and tungsten.

EXAMPLE IV

Dense particulate enzymic lactase catalyst particles have also been prepared by another method as follows: Solution A is prepared by dissolving 0.2 gm of cellulose triacetate in 7 ml of dichloromethane; Solution B is prepared by dissolving 0.04 gm of Wallerstein LP lactase in 1 ml of citrate-phosphate buffer (pH=3.0). Solution B is added to solution A and stirred to emulsify the mixture. During stirring 1 ml of glycerol and 0.4 gm of stainless steel particles are added; stirring is continued for about 15 min. The resulting mixture is extruded dropwise through a small-bore conduit into a coagulating bath of toluene. The toluene is decanted from the resulting enzyme containing particles which are then dried in air and stored in a citrate phosphate buffer under refrigeration until use. These catalyst particles contain lactase and stainless steel particles imbedded in a spherical matrix of cellulose acetate and display activities of about 200 LU/gm. A similar emulsion - coagulation technique may be used to prepare particles containing whole cells in an aqueous phase within a polymer phase.

The enzymic catalysts of this example are ideally suited for application in fluidized-bed reactors and may be extended to a wide variety of enzymes, solvents, polymers, densifying particles and emulsifying-coagulating systems. They are simple to prepare and display good stability.

EXAMPLE V

Dense, particulate immobilized amyloglucosidase [food grade Amigase (R) 200 obtained from the Wallerstein Company] was prepared using as supports particles of stainless steel and alumina as in Examples I–III and using substantially the same preparation methods of Examples I–III. Results were as follows:

| SUPPORT | pH | ENZYME SOLUTION CONCENTRATION | ENZYME SOLUTION PROPORTION | GLUTARALDEHYDE SOLUTION PROPORTION* | RESULTING** ACTIVITY |
|---|---|---|---|---|---|
| stainless Steel*** | 3.0 | 20 mg/ml | 5 ml/gm | 5 ml/gm | 1.05 units/gm |
| stainless steel | 3.0 | " | " | none | 24.4 units/gm |
| alumina | 3.0 | " | 10 ml/gm | 10 ml/gm | 62.1 units/gm |

*concentration of glutaraldehyde solution was 5% by weight
**one unit of enzymic activity corresponds to the liberation of 1$\mu$ mole of glucose per minute from a 100 mg/ml solution of maltose at 37° C and pH=4.5
*stainless steel marked * in this example was treated with water and $TiCl_4$ by the same procedure as Example I, before contacting with enzyme solution.

The fluidized- or expanded-bed reactors in which enzyme-bearing catalytic particles are maintained in a state of agitation and suspension, and in many cases caused to mix or circulate within the reaction zone, by the flow of liquid, as set forth in the present invention, can be used for a variety of chemical processing applications. For example, the reactor systems of the present invention can be used for converting starch to glucose, for inverting sugars, for oxidizing glucose, for decomposing urea or hydrogen peroxide, for lysing lipids, proteins, peptides and other molecules, for dehydrogenating alcohol, for oxidizing lipids, and for many other uses. They should find application for carrying out any enzyme-catalyzed reaction for which the enzyme can be immobilized on a solid, particulate carrier material.

Having fully described the invention, it will be apparent to one having ordinary skill in the art that many modifications and changes can be made without departing from the spirit or scope thereof. For example it is possible to carry out the present invention for many different types of enzyme-catalyzed reactions, using reactors of many different types of construction and mechanical design and by preparing many different kinds of enzyme-bearing particles of appropriate small particle size and high density suitable for use in such reactors. It is also possible to carry out the present invention while simultaneously removing particles of insolubilized-enzyme catalyst from the reactor, regenerating said catalyst particles in a separate vessel and returning said regenerated catalyst particles to the reactor.

What is claimed is:

1. An improved method of effecting enzymatic reactions in a reactant material which is contained in a carrier fluid by passing the carrier fluid past enzyme material attached by adsorption to a supporting material comprising:
    a. passing the carrier fluid generally upwardly through a reaction zone containing finely divided particles of supporting material having a size range of about 0.01 millimeters to 5 millimeters and a density of from about 2.4 to 25 grams/cm³ to which the enzyme material is attached by adsorption, the volume of the reaction zone being sufficient to contain all of the particulate supporting material in at least an expanded condition wherein the various particles are substantially not supported upon each other,
    b. maintaining an upward velocity of carrier fluid through said reaction zone sufficient to suspend and agitate the said particulate supporting material, but insufficient to carry said particulate supporting material from said reaction zone.

2. The method of claim 1 wherein the said particles of supporting material to which the enzyme material is attached by adsorption have also been treated with a bifunctional reagent in order to cross link the adsorbed enzyme material.

3. The method of claim 2 in which the said enzyme is lactase.

4. The method of claim 3 wherein the said particulate support material is essentially alumina.

5. The method of claim 3 wherein said reactant material is lactose and said carrier fluid is whey.

6. The method of claim 2 wherein said particulate supporting material is prepared by adding a hydrolyzable metal salt to an aqueous suspension of said particles thereby causing an insoluble oxide of said metal to be deposited on said particles, and contacting said particles with a solution of enzyme material in order to adsorb enzyme on said particles.

7. The method of claim 6 wherein the said enzyme is amyloglucosidase.

8. The method of claim 2 wherein said particulate supporting material is prepared by adding a hydrolyzable metal salt to an aqueous suspension of said particles thereby causing an insoluble oxide of said metal to be deposited on said particles, and contacting said particles with a solution of enzyme material in order to adsorb enzyme on said particles.

9. The method of claim 8 wherein the said enzyme is amyloglucosidase.

10. The method of claim 1 wherein said particulate supporting material is prepared by adding a hydrolyzable metal salt to an aqueous suspension of said particles thereby causing an insoluble oxide of said metal to be deposited on said particles, and contacting said particles with a solution of enzyme material in order to adsorb enzyme on said particles.

11. The method of claim 10 wherein the said enzyme is amyloglucosidase.

12. The method of claim 1 wherein the said enzyme is lactase.

13. The method of claim 12 wherein the said particulate support material is essentially alumina.

14. The method of claim 12 wherein said reactant material is lactose and said carrier fluid is whey.

* * * * *